(12) United States Patent
Yao et al.

(10) Patent No.: US 7,737,175 B2
(45) Date of Patent: Jun. 15, 2010

(54) METHODS AND COMPOSITIONS FOR REGULATING HDAC4 ACTIVITY

(75) Inventors: Tso-Pang Yao, Chapel Hill, NC (US); Todd Cohen, Durham, NC (US); Tomasa Barrientos De Renshaw, Hillsborough, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 12/130,394

(22) Filed: May 30, 2008

(65) Prior Publication Data

US 2008/0312175 A1 Dec. 18, 2008

Related U.S. Application Data

(60) Provisional application No. 60/932,735, filed on Jun. 1, 2007.

(51) Int. Cl.
*A61K 31/40* (2006.01)
*A61K 31/19* (2006.01)
*A61K 31/16* (2006.01)

(52) U.S. Cl. ............... 514/422; 514/557; 514/570; 514/575; 514/617

(58) Field of Classification Search .......... 514/422, 514/557, 570, 575, 617
See application file for complete search history.

(56) References Cited

U.S. PATENT DOCUMENTS

| | | | |
|---|---|---|---|
| 6,541,661 B1 | 4/2003 | Delorme et al. | |
| 6,673,587 B1 | 1/2004 | Evans et al. | |
| 6,706,686 B2 * | 3/2004 | Long et al. | 514/10 |
| 6,809,118 B2 * | 10/2004 | Chung | 514/570 |
| 7,229,963 B2 | 6/2007 | Sartorelli et al. | |
| 7,557,141 B2 | 7/2009 | Mishra et al. | |
| 2003/0082666 A1 | 5/2003 | Kammer et al. | |
| 2003/0144340 A1 * | 7/2003 | Long et al. | 514/422 |
| 2003/0148970 A1 | 8/2003 | Besterman et al. | |
| 2003/0152557 A1 | 8/2003 | Besterman et al. | |
| 2003/0206946 A1 * | 11/2003 | Chung | 424/450 |
| 2004/0024067 A1 | 2/2004 | Remiszewski et al. | |
| 2004/0077083 A1 | 4/2004 | Watt | |
| 2004/0077084 A1 | 4/2004 | Watt | |
| 2005/0014839 A1 | 1/2005 | Kozikowski et al. | |
| 2006/0030626 A1 | 2/2006 | Kammer et al. | |
| 2006/0178437 A1 | 8/2006 | Kammer et al. | |
| 2007/0207950 A1 | 9/2007 | Yao et al. | |
| 2009/0076021 A1 | 3/2009 | Plato | |
| 2009/0118291 A1 | 5/2009 | Belvedere et al. | |
| 2009/0181943 A1 | 7/2009 | Tessier et al. | |

FOREIGN PATENT DOCUMENTS

| | | |
|---|---|---|
| WO | WO 03/033678 A2 | 4/2003 |
| WO | WO 03/076430 A1 | 9/2003 |
| WO | WO/2006026260 A1 | 3/2006 |
| WO | WO 2007/100795 A2 | 9/2007 |

OTHER PUBLICATIONS

Adams and Goldman. "Role for Calcium From the Sarcoplasmic Reticulum in Coupling Muscle Activity to Nicotinic Acetylcholine Receptor Gene Expression in Rat" *J Neurobiol* 35:245-257 (1998).
Backs et al. "CaM Kinase II Selectively Signals to Histone Deacetylase 4 During Cardiomyocyte Hypertrophy" *The Journal of Clinical Investigation* 116(7):1853-1864 (2006).
Banks et al. "The Postsynaptic Submembrane Machinery at the Neuromuscular Junction: Requirement for Rapsyn and the Utrophin/Dystrophin-Associated Complex" *Journal of Neurocytology* 32:709-726 (2003).
Bassel-Duby and Olson. "Signaling Pathways in Skeletal Muscle Remodeling" *Annu Rev Biochem* 75:19-37 (2006).
Bessereau et al. "In Vivo and In Vitro Analysis of Electrical Activity-Dependent Expression of Muscle Acetylcholine Receptor Genes Using Adenovirus" *Proc Natl Acad Sci USA* 91:1304-1308 (1994).
Blake et al. "Utrophin: A Structural and Functional Comparison to Dystrophin" *Brain Pathol* 6(1):37-47 (1996) (Abstract Only).
Bodine et al. "Identification of Ubiquitin Ligases Required for Skeletal Muscle Atrophy" *Science* 294:1704-1708 (2001).
Bolger and Yao. "Intracellular Trafficking of Histone Deacetylase 4 Regulates Neuronal Cell Death" *The Journal of Neuroscience* 25(41):9544-9553 (2005).
Bolger et al. "The Neurodegenerative Disease Protein Ataxin-1 Antagonizes the Neuronal Survival Function of Myocyte Enhancer Factor-2" *Journal of Biological Chemistry* 282(40):29186-29192 (2007).
Cohen et al. "The Histone Deacetylase HDAC4 Connects Neural Activity to Muscle Transcriptional Reprogramming" *Journal of Biological Chemistry* 282(46):33752-33759 (2007).

(Continued)

*Primary Examiner*—Raymond J Henley, III
(74) *Attorney, Agent, or Firm*—Myers Bigel Sibley & Sajovec, P.A.

(57) ABSTRACT

The present invention provides methods and compositions for modulating HDAC4 activity and modulating the activity of proteins downstream of HDAC4 in the muscle transcriptional pathway in a cell by modulating HDAC4 activity. Further provided are methods and compositions for treating muscle atrophy and/or inflammation by inhibiting HDAC4 activity.

20 Claims, 2 Drawing Sheets

OTHER PUBLICATIONS

Cohen et al. "The Histone Deacetylase HDAC4 Links Neural Activity to Transcriptional Reprogramming" Poster presentation at Gordon Research Conference entitled "Myogenesis," Lucca, Italy (May 13-18, 2007).

Cox et al. "Identification of the Mouse Neuromuscular Degeneration Gene and Mapping of a Second Site Suppressor Allele" *Neuron* 21:1327-1337 (1998).

Grady et al. "Maturation and Maintenance of the Neuromuscular Synapse: Genetic Evidence for Roles of the Dystrophin-Glycoprotein Complex" *Neuron* 25:279-293 (2000).

Gundersen et al. "Overexpression of Myogenin in Muscles of Transgenic Mice: Interaction with Id-1, Negative Crossregulation of Myogenic Factors, and Induction of Extrasynaptic Acetylcholine Receptor Expression" *Molecular and Cellular Biology* 15(12):7127-7134 (1995).

Huang and Schmidt. "Calcium Influx Blocks the Skeletal Muscle Acetylcholine Receptor α-Subunit Gene in Vivo" *FEBS Letters* 338:277-280 (1994).

Klarsfeld and Changeux. "Activity Regulates the Levels of Acetylcholine Receptor α-Subunit mRNA in Cultured Chicken Myotubes" *Proc Natl Acad Sci USA* 82:4558-4562 (1985).

Lu et al. "Signal-Dependent Activation of the MEF2 Transcription Factor by Dissociation From Histone Deacetylases" *Proc Natl Acad Sci USA* 97(8):4070-4075 (2000).

MacPherson et al. "Activity-Dependent Gene Regulation in Conditionally-Immortalized Muscle Precursor Cell Lines" *Journal of Cellular Biochemistry* 91:821-839 (2004).

MacPherson et al. "Myogenin-Dependent nAChR Clustering in Aneural Myotubes" *Mol Cell Neurosci* 31:649-660 (2006).

MacPherson et al. "Protein Kinase C and Calcium/Calmodulin-Activated Protein Kinase II (CaMK II) Suppress Nicotinic Acetylcholine Receptor Gene Expression in Mammalian Muscle" *The Journal of Biological Chemistry* 277(18):15638-15646 (2002).

Maddatu et al. "Transgenic Rescue of Neurogenic Atrophy in the *nmd* Mouse Reveals a Role for *Ighmbp2* in dilated Cardiomyopathy" *Human Molecular Genetics* 13(11):1105-1115 (2004).

McKinsey et al. "Identification of a Signal-Responsive Nuclear Export Sequence in Class II Histone Deacetylases" *Molecular and Cellular Biology* 21(18):6312-6321 (2001).

McKinsey et al. "Signal-Dependent Nuclear Export of a Histone Deacetylase Regulates Muscle Differentiation" *Nature* 408:106-111 (2000).

Mejat et al. "Histone Deacetylase 9 Couples Neuronal Activity to Muscle Chromatin Acetylation and Gene Expression" *Nature Neuroscience* 8(3):313-321 (2005).

Mejat et al. "Synapse-Specific Gene Expression at the Neuromuscular Junction" *Ann NY Acad Sci* 998:53-65 (2003).

Merlie et al. "Myogenin and Acetylcholine Receptor α Gene Promoters Mediate Transcriptional Regulation in Response to Motor Innervation" *The Journal of Biological Chemistry* 269(4):2461-2467 (1994).

Neville et al. "Kinetics of Expression of Ach Receptor Alpha-Subunit mRNA in Denervated and Stimulated Muscle" *Neuroreport* 2(11):655-657 (1991) (Abstract Only).

Sanes and Lichtman. "Development of the Vertebrate Neuromuscular Junction" *Annu Rev Neurosci* 22:389-442 (1999).

Sanes and Lichtman. "Induction, Assembly, Maturation and Maintenance of a Postsynaptic Apparatus" *Neuroscience* 2:791-805 (2001).

Schaeffer et al. "Targeting Transcription to the Neuromuscular Synapse" *Neuron* 31:15-22 (2001).

Siu et al. "Hindlimb Unloading Increases Muscle Content of Cytosolic but Not Nuclear Id2 and p53 Proteins in Young Adult and Aged Rats" *J Appl Physiol* 100:907-916 (2006).

Su et al. "The Depolarization Response Element in Acetylcholine Receptor Genes is a Dual-Function E Box" *FEBS Letters* 366:131-136 (1995).

Tang and Goldman. "Activity-Dependent Gene Regulation in Skeletal Muscle is Mediated by a Histone Deacetylase (HDAC)-Dach2-Myogenin Signal Transduction Cascade" *Proc Natl Acad Sci USA* 103(45):16977-16982 (2006).

Tang et al. "CaM Kinase II-Dependent Phosphorylation of Myogenin Contributes to Activity-Dependent Suppression of nAChR Gene Expression in Developing Rate Myotubes" *Cellular Signalling* 16:551-563 (2004).

Tang et al. "Separate Pathways for Synapse-Specific and Electrical Activity-Dependent Gene Expression in Skeletal Muscle" *Development* 120:1799-1804 (1994).

Walke et al. "Identification and Characterization of a 47 Base Pair Activity-Dependent Enhancer of the Rat Nicotinic Acetylcholine Receptor δ-Subunit Promoter" *The Journal of Neuroscience* 16(11):3641-3651 (1996).

Wu et al. "Regulation of Mitochondrial Biogenesis in Skeletal Muscle by CaMK" *Science* 296:349-352 (2002).

Zhao et al. "The Modular Nature of Histone Deacetylase HDAC4 Confers Phosphorylation-Dependent Intracellular Trafficking" *The Journal of Biological Chemistry* 276(37):35042-35048 (2001).

Beck et al. "Phase I Pharmacokinetic (PK) and Pharmacodynamic (PD) Study of LBH589A: A Novel Histone Deacetylase Inhibitor" *Journal of Clinical Oncology*, 2004 ASCO Meetings Proceedings v22, Jul. 15, 2004 (Abstract Only) (2 pages).

Cohen and Yao. "AcK-Knowledge Reversible Acetylation" *Sci STKE* 245:1-3 (pe42)(2004).

Cohen et al. "The Deacetylase HDAC4 Controls Myocyte Enhancing Factor-2-Dependent Structural Gene Expression in Response to Neural Activity" *FASEB J* 23:99-106 (2009) (Abstract only).

Office Action issued for U.S. Appl. No. 11/643,295, mailed Oct. 28, 2008.

Office Action issued for U.S. Appl. No. 11/643,295, mailed Aug. 5, 2009.

PCT Application No. PCT/US2009/063905, filed Nov. 10, 2009, entitled "Methods of Inhibiting Cancer Cell Growth with HDAC Inhibitors and Methods of Screening for DHAC10 Inhibitors" Inventors: Tso-Pang Yao et al.

Guardiola and Yao. "Molecular Cloning and Characterization of a Novel Histone Deacetylace HDAC10" *The Journal of Biological Chemistry* 277(5):3350-3356 (2002).

Kovacs at al. "The HDAC Complex and Cytoskeleton" *Novartis Found Symp* 259:170-181 (2004).

Kovacs et al. "HDAC6 Regulates Hsp90 Acetylation and Chaperone-Dependent Activation of Glucocorticoid Receptor" *Molecular Cell* 18:601-607 (2005).

Kozhemyakina et al. "Parathyroid Hormone-Related Peptide Represses Chondrocyte Hypertrophy Through a Protein Phosphatase 2A/Histone Deacetlase 4/MEF2 Pathway" *Molecular and Cellular Biology* 29(21):5751-5762 (2009).

Nakamura et al. "Inhibition of Histone Deacetylase Suppresses Osteoclastogenesis and Bone Destruction by Inducing IFN-α Production " *The Journal of Immunology* 175:5809-5816 (2005).

R&D Focus Drug News, newsletter dated Dec. 8, 2003 (1 page).

\* cited by examiner

METHODS AND COMPOSITIONS FOR REGULATING HDAC4 ACTIVITY

STATEMENT OF PRIORITY

This application claims the benefit, under 35 U.S.C. §119 (e), of U.S. Provisional Application No. 60/932,735, filed Jun. 1, 2007, the entire contents of which are incorporated by reference herein.

FIELD OF THE INVENTION

The present invention provides methods for modulating HDAC4 activity and modulating the activity of proteins downstream of HDAC4 in the muscle transcriptional pathway in a cell by modulating HDAC4 activity.

BACKGROUND OF THE INVENTION

Skeletal muscle activity is regulated by electrical signals propagated by motor neurons which innervate muscle at the neuromuscular junction (NMJ), a specialized synapse structure (1). Nicotinic acetylcholine receptors (nAChRs) positioned on the post-synaptic membrane of NMJ are central in mediating nerve-muscle communication (2). As such, nAChRs are regulated at both transcriptional and post-translational levels in response to neural activity. Neural input affects NMJ stability and function through multiple mechanisms (1). First, the nerve secreted protein agrin induces nAChR clustering through activation of a MUSK/rapsyn/nAChR complex, which engages the cytoskeleton and provides an extremely high local density of nAChR at the NMJ (3, 4). Members of the Dystrophin-Glycoprotein complex (DGC) are critical in providing stability and maintenance of the synapse (5, 6). Second, nAChR gene expression is induced specifically in sub-synaptic nuclei located beneath the post-synaptic apparatus by the transcription factor GABP, a process which acts to locally deposit activity-dependent factors at the NMJ, including nAChR, MUSK, and structural proteins (7, 8). Finally, to exclude the expression of nAChR subunits in extra-synaptic regions, activity-mediated calcium efflux activates calcium-dependent enzymes, such as calcium-dependent protein kinase II (CaMKII) (9-12), which through a yet to be characterized pathway, down-regulates myogenin expression and therefore inhibits nAChR expression as a consequence. In conjunction, these three processes account for much of the synaptic accumulation of nAChRs.

Conversely, reduced neural activity by surgical denervation, inactivity or neuromuscular defects associated with pathological conditions, such as Amyotrophic Lateral Sclerosis (ALS), can lead to extrasynaptic expression of nAChR induced by the bHLH transcription factor myogenin (MGN) (13). Such activation of transcription similarly occurs during embryonic muscle development before innervation, leading to high level expression of nAChR subunits throughout the muscle. The increased levels of AChR result in acetylcholine super-sensitivity, which is thought to be important for successful formation of muscle synapse after innervation. This induction of nAChR is mediated by myogenin, which binds E-box elements (CANNTG) present in the promoters of activity-regulated genes including nAChRε, nAChRδ and MUSK (14-19). Myogenin gene expression is repressed by Dachschund related transcriptional co-repressor, Dach2 (20). Interestingly, Dach2 expression itself is suppressed by denervation, suggesting a model whereby reduction of Dach2 causes transcriptional induction of myogenin and subsequent activation of nAChR (20).

Myofibers are grossly classified into slow/oxidative fibers and fast/glycolytic fibers that are distinct in contractile velocity and metabolic properties. The slow/oxidative fibers are slow in twitching but more resistant to fatigue. Metabolically, they are rich in mitochondria, and use oxidative phosphorylation to provide ATP for contraction (thus termed oxidative fibers). The fast/glycolytic fibers, in contrast, are fast in contractility but prone to fatigue. They contain fewer mitochondria and use glycolysis as the main source of energy (Spangenburg E E, Booth F W. *Acta Physiol Scand*. (2003) 178(4): 413-24). In addition to contractile properties, these fibers also differ in their capacity in glucose metabolism with slow/oxidative fibers being more responsive to insulin than fast/glycolytic fibers. Thus, the composition of myofibers is not only critical for performing different movements but also important for regulating glucose metabolism.

The functionality of a myofiber is determined by the expression of unique sets of contractile proteins and metabolic enzymes at the transcriptional level. For example, in slow fibers, type I MHC is the dominant form of myosin heavy chain while in fast fiber, type IIb or IIx MHC are the main isotypes (Spangenburg E E, Booth F W. *Acta Physiol Scand*. (2003) 178(4):413-24). On the metabolic end, the differential expression of the transcriptional co-activator PGC-1α, which promotes mitochondrion biogenesis, likely plays a critical role (Lin J et al., *Cell Metab*. (2005) 1(6):361-70). Thus, PGC-1α is expressed at a higher level in mitochondrion-rich slow/oxidative fibers than in fast/glycolytic fibers. In fact, over-expression of PGC-1α is sufficient to convert fast/glycolytic fibers to slow/oxidative fibers in a mouse model (Lin J. et al., *Nature*. (2002) 418(6899):797-801).

Uniquely, the adult myofiber phenotype is not permanent. The size, contractility and metabolic property of myofibers can all undergo changes or remodeling (Talmadge R J. *Muscle Nerve*. (2000) 23(5):661-79). For example, reduced neuromuscular activity caused by inactivity, ageing or neuromuscular disease can lead to reduction in muscle size, termed atrophy. Interestingly, inactivity also causes an increase in fast/glycolytic fibers. Conversely, repetitive use, such as exercise training, induces muscle hypertrophy and a concomitant increase in oxidative/slow fiber. These coordinated changes allow muscle to perform different tasks and meet different functional demands. This remarkable adaptability of skeletal muscle is achieved by a highly regulated gene transcription program, which in response to differential neuromuscular activities, controls myofiber size, contractility and metabolism. This so called "neural activity-dependent muscle remodeling" is essential for muscle function and homeostasis.

Temporary reduction in muscle size is part of normal remodeling in responses to reduced neural activity. However, chronically reduced neural activities associated with neuromuscular disease, aging and denervation can cause muscle atrophy, a muscle wasting disease characterized by an excessive reduction in muscle size and strength. In neuromuscular diseases, such as Amyotrophic Lateral Sclerosis (ALS), motor neuron dysfunction leads to severe muscle atrophy in both diaphragm and limbs, contributing to breathing and moving difficulty and eventual death. The loss of muscle mass in atrophy is, at least in part, due to accelerated protein degradation catalyzed by two ubiquitin E3 ligases, atrogin-1/MAFbx and MuRF1, both of which are induced transcriptionally in atrophic muscle (Bodine S C, et al., *Science*. (2001) 294(5547):1704-8); Gomes M D, et al, *Proc Natl Acad Sci USA*. (2001) 98(25): 14440-5). Although the detailed mechanism remains uncertain, Atrogin-1 and MURF1 were proposed to promote atrophy by degrading structural and contractile proteins, such as myosin light chain, myotilin, myomesin and titin (Witt S H, et al., *J Mol Biol.* 2005; 350 (4):713-22). Interestingly, gene array analysis revealed that the same set of genes is also transcriptionally repressed in atrophic muscle (Bodine S C, et al., *Science.* (2001) 294 (5547):1704-8). These observations indicate that the atrophy-associated decrease in structural and contractile proteins might be achieved through both active protein degradation and transcriptional repression caused by reduced neural activity. Identifying the transcriptional pathway responsible for atrophy-associated gene repression could provide new therapeutic opportunity for this devastating disease.

Pathological muscle remodeling has also been implicated in the development of metabolic disease. A decrease in oxidative/slow and an increase in glycolytic/fast fibers have been reported in patients with type II diabetes (Oberbach A, et al., *Diabetes Care.* (2006) 29(4):895-900). Indeed, aging and inactivity, which are both associated with the development of insulin resistance, also lead to diminished oxidative capacity of skeletal muscle. Conversely, an increase in slow/oxidative fibers by exercise training enhances insulin sensitivity (Oberbach A, et al., *Diabetes Care.* (2006) 29(4):895-900). Thus, the composition of myofibers is important for regulating glucose metabolism. A pharmacological means of stimulating oxidative fiber formation in muscle—an ability to control fiber type specification by manipulating the muscle-remodeling program—could have the potential to increase insulin sensitivity and thereby provide therapeutic benefits to patients with type II diabetes. Elucidating the transcriptional network that coordinately controls myofiber type and size would be a key toward the development of and effective therapeutic strategy.

Six histone deacetylases have been identified in mammalian cells, the yeast RPD3 homologs HDAC1, HDAC2 and HDAC3 and the yeast HDA1 homologs HDAC4/HDAC-A, HDAC5 and HDAC6.

Histone deacetylase 4 (also known as HDAC4 and HDAC-A) was the first HDA1 homolog to be identified (Fischle et al., *J. Biol. Chem.*, 274:11713-11720 (1999); Grozinger et al., *Proc. Natl. Acad. Sci. USA*, 96:4868-4873 (1999); Miska et al., *Embo J.*, 18:5099-5107 (1999)). Unlike the other histone deacetylases, histone deacetylase 4 contains a noncatalytic N-terminal domain through which it can interact with specific transcription factors. When tethered to a promoter, histone deacetylase 4 has been shown to represses transcription through two independent repression domains, with repression domain 1 consisting of the N-terminal 208 residues and repression domain 2 containing the deacetylase domain found in the C-terminus (Wang et al., *Mol. Cell. Biol.*, 19:7816-7827 (1999)).

Another unique feature described for histone deacetylase 4, involves its cellular localization. The protein shuttles between the nucleus and cytoplasm in a process involving active transport. In the nucleus, through a small region located at its N-terminal domain, histone deacetylase 4 interacts with two MADS-box transcription factors, MEF2A (Miska et al., *Embo J.*, 18:5099-5107 (1999)) and MEF2C (Wang et al., *Mol. Cell. Biol.*, 19:7816-7827 (1999)). Furthermore, histone deacetylase 4 and MEF2C individually upregulate but together downmodulate c-jun promoter activity. These results indicate that HDAC4 interacts with transcription factors such as MEF2C and MEF2A to negatively regulate gene expression. Co-immunoprecipitation data demonstrated that histone deacetylase 4 does not interact with either the NURD or mSin3A complexes as do other histone deacetylases (Grozinger et al., *Proc. Natl. Acad. Sci. USA*, 96:4868-4873 (1999)). However, it has been found in association with other proteins (Fischle et al., *J. Biol. Chem.*, 274:11713-11720 (1999)).

Huang et al. have shown that histone deacetylase 4 represses transcription by interacting with the conserved non-redundant repression domains (RDs) found in the corepressors, N-CoR and SMRT. These corepressors play a critical in the function of nuclear hormone receptors, and are deregulated in human myeloid leukemias. Endogenous N-CoR and SMRT each associate with HDAC4 in a complex that does not contain mSin3A or HDAC1. These results indicate that alternative histone deacetylase complexes may mediate specific repression pathways in normal as well as leukemic cells (Huang et al., *Genes Dev.*, 14:45-54 (2000)).

Histone deacetylase 4 (HDAC4) is expressed in various adult human tissues, with the highest levels of expression found in skeletal muscle, thymus and small intestine and very low levels found in liver, placenta and kidney (Fischle et al., J. Biol. Chem., 1999, 274, 11713-11720).

SUMMARY OF THE INVENTION

The present invention is based on studies that demonstrate that HDAC4 is a regulator of muscle (e.g., skeletal muscle) transcriptional reprogramming. Thus, the present invention provides methods for modulating HDAC4 activity and modulating the activity of proteins downstream of HDAC4 in the muscle transcriptional pathway in a cell by modulating HDAC4 activity.

One aspect of the present invention provides a method of increasing slow/oxidative fiber formation in skeletal muscles, comprising contacting skeletal muscle cells with an inhibitor of HDAC4 activity.

A further aspect of the present invention is a method of modulating muscle remodeling signaling in a cell, comprising contacting the cell with an inhibitor of HDAC4 activity.

In addition, the present invention provides a method of increasing peroxisome proliferator-activated receptor-γ coactivator (PGC)-1α expression in a cell, comprising contacting the cell with an inhibitor of HDAC4 activity.

Also provided herein is a method of decreasing muscle-specific RING finger protein 1 (MuRF1) expression in a cell, comprising contacting the cell with an inhibitor of HDAC4 activity.

A further aspect of the present invention is a method of increasing Dachschund 2 (Dach 2) activity in a cell, comprising contacting the cell with an inhibitor of HDAC4 activity.

A further aspect of the present invention is a method of decreasing myogenin activity in a cell, comprising contacting the cell with an inhibitor of HDAC4 activity.

A further aspect of the present invention is a method of decreasing nicotinic acetylcholine receptor (nAChR) alpha, beta, and/or gamma subunit expression in a muscle cell, comprising contacting the cell with an inhibitor of HDAC4 activity.

A further aspect of the present invention is a method of treating muscular atrophy (e.g., skeletal muscular atrophy) in a subject, comprising administering to the subject an effective amount of an inhibitor of HDAC4 activity.

A further aspect of the present invention is a method of treating diabetes in a subject, comprising administering to the subject an effective amount of an inhibitor of HDAC4 activity.

A further aspect of the present invention is a method of treating insulin resistance in a subject, comprising administering to the subject an effective amount of an inhibitor of HDAC4 activity.

A further aspect of the present invention is a method of increasing insulin sensitivity in a subject, comprising administering to the subject an effective amount of an inhibitor of HDAC4 activity.

DETAILED DESCRIPTION OF THE INVENTION

Figure 1:
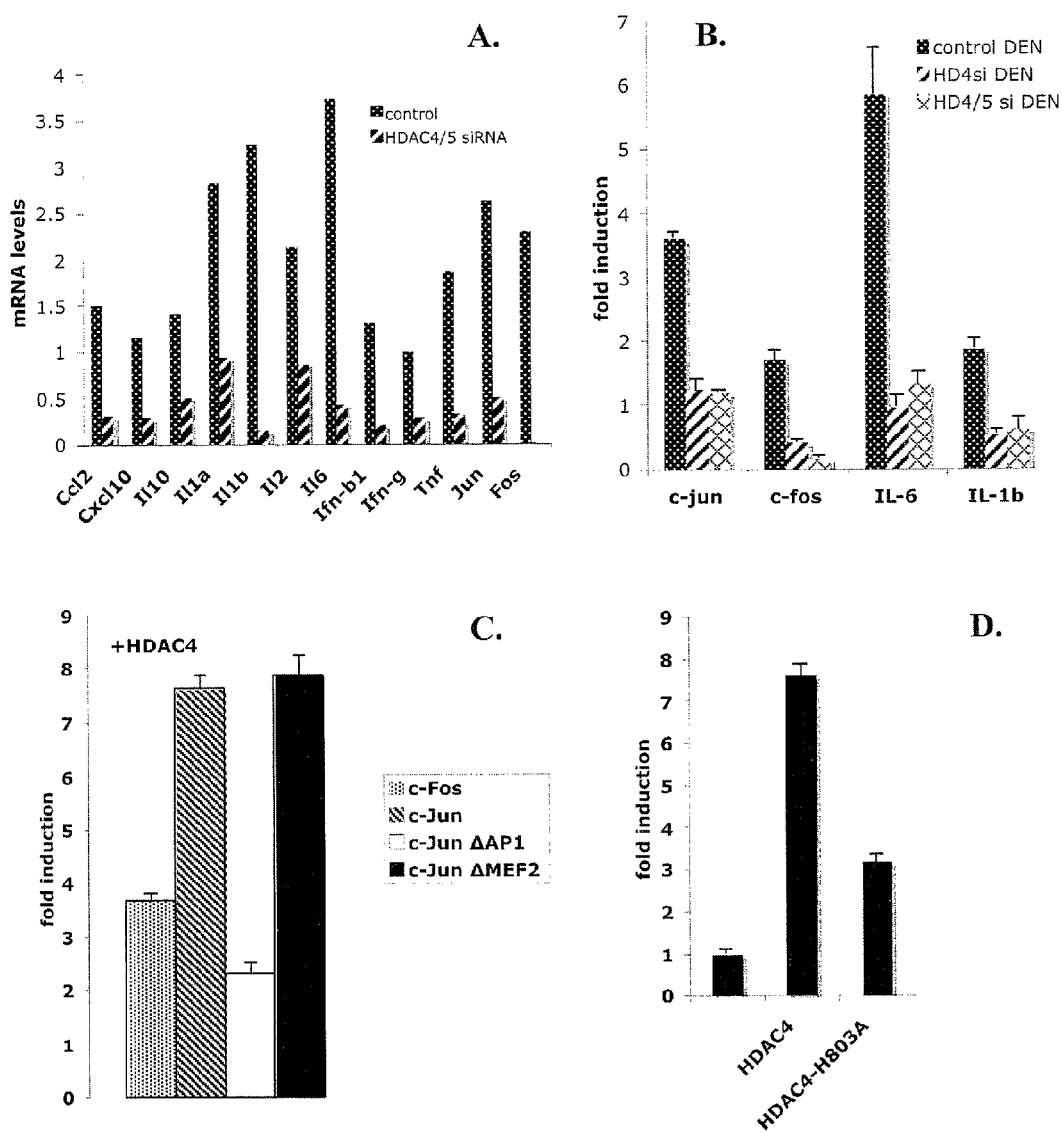
FIGS. 1A-D. Expression of genes involved in inflammation. A. A real-time RT-PCR superarray was used to determine whether inflammatory gene expression is regulated by class IIA HDACs 4/5. RNA from control denervated and HDAC4/5 siRNA electroporated denervated muscles was analyzed for expression of ~90 key inflammatory genes and plotted as fold induction. B. The levels of IL-1beta and Il-6 in control-denervated and HDAC4/5 siRNA transfected denervated muscles were analyzed by real-time PCR. C. Activation of c-fos and c-jun expression by elevated levels of HDAC4 was evaluated. D. HDAC4 enzymatic activity is shown to be required for the activation of c-jun transcription.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

As used herein, "a" or "an" or "the" can mean one or more than one. For example, "a" cell can mean one cell or a plurality of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of 20%, 10%, 5%, 1%, 0.5%, or even 0.1% of the specified amount.

In one embodiment provided herein, the present invention provides a method of inhibiting histone deacetylase 4 (HDAC4) activity. Such inhibition of HDAC4 activity can be used, e.g., in a method of treating a neurodegenerative disease and/or diabetes. As used herein, "inhibit" or "inhibiting" means to partially or completely block a particular process or activity. For example, a compound inhibits skeletal muscle atrophy if it either completely or partially prevents muscle atrophy.

A cell of this invention can be any cell with HDAC4 activity. Such a cell can be in vitro, ex vivo and/or in vivo. Nonlimiting examples of a cell line of this invention include A549 lung carcinoma cells, kidney 293 cells, HeLa cervical carcinoma cells and COS-7 monkey kidney cells.

A cell of this invention can be a cell in a subject of this invention and such a cell can be any cell in the subject with HDAC4 activity. A subject of this invention can be any animal that produces HDAC4. A subject of this invention can also be a subject in need of the methods of treatment provided herein (e.g., a subject with diabetes and/or muscle atrophy, as well as a subject at risk of developing diabetes and/or muscle atrophy). Nonlimiting examples of a subject of this invention include mammals such as humans, mice, dogs, cats, horses, cows, rabbits, goats, etc.

As used herein, "skeletal muscle" refers to a type of striated muscle, usually attached to the skeleton of a subject, which consists of skeletal muscle tissue, connective tissue, nerve tissue, and blood or vascular tissue.

Suitable skeletal muscle tissue can include but is not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor and any other suitable skeletal muscle as known in the art.

Also as used herein, the terms "muscle" and "muscle cell" include skeletal muscle, cardiac muscle, diaphragm muscle, smooth muscle, myoblasts, myotubes, myofibers and the like as are well known in the art.

As used herein, "muscular atrophy" or "skeletal muscle atrophy" means "muscle wasting" and refers to a decrease in skeletal muscle mass or skeletal muscle function or both.

In some embodiments, muscular atrophy is associated with a genetic disorder (e.g., a muscular dystrophy, a neurodegenerative disorder), a neuromuscular disorder, autoimmune disease, infectious disease (e.g., HIV infection, tuberculosis), acquired immunodeficiency syndrome (AIDS); cachexia; inactivity (e.g., disuse due to surgery, bed rest, broken bones, immobilizations, including, but not limited to, those accompanying an orthopedic procedure, etc.), ageing (e.g., sarcopenia), cancer, denervation/nerve damage (e.g., due to spinal cord injury), glucocorticoid use for unrelated conditions; sepsis due to infection or other causes; nutrient limitation due to illness or starvation; space travel, chronic inflammation, chronic obstructive pulmonary disease (COPD), congestive heart failure and any combination thereof. In some embodiments, muscular atrophy is associated with, but not limited to, amyotrophic lateral sclerosis (also known as Lou Gehrig's disease), spinal muscular atrophy and/or spinal muscular atrophy with respiratory distress type 1 (SMARD1).

As referred to herein, muscular atrophy can be associated with, but is not limited to, Parkinson's disease, Alzheimer's disease, amyotrophic lateral sclerosis (ALS, also known as Lou Gehrig's disease), chronic granulomatous disease, Huntington's disease, Gaucher's disease, galactosialidosis, atherosclerosis and other neurodegenerative diseases now known or later identified that can be treated according to the methods of this invention.

As referred to herein, muscular atrophy can be associated with, but is not limited to muscular dystrophies including, but not limited to, Becker's muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, and oculopharyngeal muscular dystrophy.

As referred to herein, muscular atrophy can be associated with, but is not limited to, neuromuscular disorders including spinal muscular atrophies (e.g., amyotrophic lateral sclerosis (ALS, or Lou Gehrig's Disease), infantile progressive spinal muscular atrophy (SMA Type 1), intermediate spinal muscular atrophy (SMA Type 2), juvenile spinal muscular atrophy (SMA Type 3), and adult spinal muscular atrophy (SMA Type 4)), inflammatory myopathies (e.g., dermatomyositis, polymyositis), diseases of peripheral nerves (e.g., Charcot-Marie Tooth Disease, DeJerine-Sottas Disease, Friedreich's Ataxis), diseases of neuromuscular junctions (e.g., myasthenia gravis, Lambert-Eaton Syndrome), metabolic diseases of the muscle (e.g., acid maltase deficiency, carnitine palmityl transferase deficiency, debrancher enzyme deficiency, lactate dehydrogenase deficiency, mitochondrial myopathy, myoadenylate deaminase deficiency, phosphorylase deficiency, phosphofructokinase deficiency, phosphoglycerate kinase deficiency), and other myopathies (e.g., central core disease, hyperthyroid myopathy, myotonia congenita, myotubular myopathy, nemaline myopathy, paramyotonia congenita, periodic paralysis, hypokalemic, hyperkalemic).

As referred to herein, muscular atrophy can be associated with autoimmune diseases, including but not limited to, diabetes mellitus type 1 (IDDM), systemic lupus erythematosus (SLE), Sjögren's syndrome, Hashimoto's thyroiditis, Graves' disease, and rheumatoid arthritis.

As used herein, HIV infection refers to HIV infection and HIV disease progression.

As used herein, acquired immunodeficiency syndrome (AIDS) refers to a collection of symptoms and infections resulting from the specific damage to the immune system caused by the human immunodeficiency virus (HIV) and HIV progression.

As used herein, cachexia refers to a loss of weight, muscle atrophy, fatigue, weakness and/or significant loss of appetite in someone who is not actively trying to lose weight, which is often associated with some underlying disorder.

A cancer associated with muscular atrophy of this invention can be, but is not limited to, B cell lymphoma, T cell lymphoma, myeloma, leukemia (AML, ALL, CML, CLL), hematopoietic neoplasias, thymoma, lymphoma, sarcoma, lung cancer, liver cancer, non-Hodgkins lymphoma, Hodgkins lymphoma, Burkitt's lymphoma, breast cancer, pancreatic cancer, colon cancer, lung cancer, renal cancer, bladder cancer, liver cancer, prostate cancer, ovarian cancer, primary or metastatic melanoma, squamous cell carcinoma, basal cell carcinoma, sebaceous cell carcinoma, brain cancer (astrocytoma, glioma, glioblastoma, ependymoma, medulloblastoma, meningioma, oligodendroglioma, oligoastrocytoma), angiosarcoma, hemangiosarcoma, adenocarcinoma, liposarcoma, head and neck carcinoma, thyroid carcinoma, soft tissue sarcoma, osteosarcoma, testicular cancer, uterine cancer, cervical cancer, gastrointestinal cancer, colorectal cancer, oral cancer, nasopharyngeal cancer, oropharyngeal cancer, esophageal cancer, stomach cancer, multiple myeloma, bile duct cancer, cervical cancer, laryngeal cancer, penile cancer, urethral cancer, anal cancer, vulvar cancer, vaginal cancer, gall bladder cancer, thymoma, salivary gland cancer, lip and oral cavity cancer, adenocortical cancer, non-melanoma skin cancer, pleura mesothelioma, joint cancer, hypopharyngeal cancer, ureter cancer, peritoneum cancer, omentum cancer, mesentery cancer, Ewing's sarcoma, rhabdomyosarcoma, spinal cord cancer, endometrial cancer, neuroblastoma, pituitary cancer, retinoblastoma, eye cancer, islet cell cancer, and any other cancer now known or later identified to be associated with muscular atrophy.

As used herein, denervation refers to loss of nerve supply, such loss being a result of a disease, a chemical (e.g., botulinum toxin), a physical injury or interruption of a nerve (e.g., due to injury/accident, to relieve pain, surgery).

In one embodiment, the present invention provides a method of increasing slow/oxidative fiber formation in a skeletal muscle of a subject, comprising contacting cells in the muscle with an inhibitor of HDAC4 activity. In some embodiments, the present invention provides a method of improving insulin resistance in a subject, said method comprising increasing slow/oxidative fiber formation in skeletal muscles of a subject by contacting cells in the muscle of the subject with an inhibitor of HDAC4 activity. Further, in some embodiments, the present invention provides a method of reducing susceptibility to muscular atrophy in a subject, said method comprising increasing slow/oxidative fiber formation in skeletal muscles of a subject by contacting cells in the muscles with an inhibitor of HDAC4 activity.

The methods of the present invention employ an inhibitor of HDAC4 activity. An inhibitor of HDAC4 activity is any compound, agent or material that has an inhibitory effect on the activity of HDAC4. An inhibitory effect means that the amount of activity of HDAC4 that is measured in an assay in the absence of an HDAC4 inhibitor is reduced when the inhibitor is added to the assay. Assays to measure HDAC4 activity are known in the art and as described herein. For example, to test HDAC4 activity, one can utilize a luciferase assay, which monitors MEF2-dependent induction of a luciferase reporter gene (23). Activated MEF2 induces the expression of a luciferase reporter, which can be readily detected in an enzymatic reaction using a luciferase substrate (e.g., luciferin). As an inhibitor of MEF2 activity, elevated levels of HDAC4 activity repress the levels of luciferase produced. In contrast, inhibition of HDAC4 activates MEF2 activity and therefore elevates the luciferase levels produced. This assay therefore provides a convenient method to rapidly and efficiently monitor the activity of HDAC4.

An inhibitor of HDAC4 activity of this invention can be but is not limited to hydroxamic acid based HDAC inhibitors, Suberoylanilide hydroxamic acid (SAHA) and its derivatives, NVP-LAQ824, LBH589, Trichostatin A, Scriptaid, m-Carboxycinnamic acid bishydroxamic acid (CBHA), ABHA, Pyroxamide, Propenamides, Oxamflatin, 6-(3-Chlorophenylureido)caproic hydroxamic acid (3-Cl-UCHA), A-161906, jnj16241199, tubacin and tubacin analogs, small interfering RNA (siRNA), short chain fatty acid HDAC inhibitors, butyrate, phenylbutyrate, valproate, hydroxamic acid, trichostatins, epoxyketone-containing cyclic tetrapeptides, HC-toxin, Chlamydocin, Diheteropeptide, WF-3161, Cyl-1, Cyl-2, non-epoxyketone-containing cyclic tetrapeptides, Apicidin, cyclic-hydroxamic-acid-containing peptides (CHAPS), benzamides and benzamide analogs, CI-994, trapoxin, deprudecin, organosulfur compounds, MS275, depsipeptide (FK2-28) and any combination thereof. In some embodiments of this invention, one or more than one inhibitor of HDAC4 in any combination can be excluded from the list of inhibitors of HDAC4 of this invention.

An inhibitor of HDAC4 activity that can be employed in the methods of this invention can be an inhibitor that acts at the level of transcription and/or translation of the HDAC4 protein, whereby such an inhibitor alters HDAC4 activity by decreasing the amount of functional HDAC4 protein produced. An inhibitor of HDAC4 activity can be, but is not limited to, an antisense nucleic acid, a ribozyme (e.g., as described in U.S. Pat. No. 5,877,022), RNAs that effect spliceosome-mediated trans-splicing (Puttaraju et al. (1999) *Nature Biotech.* 17:246; U.S. Pat. No. 6,013,487; U.S. Pat. No. 6,083,702), RNAs that trigger RNA interference mechanisms (RNAi), including small interfering RNAs (siRNA) that mediate gene silencing (Kawaguchi et al., (2003) *Cell* 115:727-738; Sharp et al. (2000) *Science* 287:2431) and/or other non-translated RNAs, such as "guide" RNAs (Gorman et al., (1998) *Proc. Nat. Acad Sci. USA* 95:4929; U.S. Pat. No. 5,869,248 to Yuan et al.), and the like, as are known in the art. These transcription/translation inhibitors can be employed in the methods of this invention individually, in combination with one another and/or in combination with other HDAC4 inhibitors of this invention. Nonlimiting examples of a siRNA (also termed shRNA) of this invention include the nucleotide sequence 5' AAACGGUGGAUGUGGCCACGG 3' (SEQ ID NO:1), the nucleotide sequence 5' AAG-GAGCUGCUGAAUCCUGCC 3' (SEQ ID NO:2), and the nucleotide sequence 5' CACCGGAACCUGAACCACUG-CAUUU 3' (SEQ ID NO 3). The production and identification of additional siRNA sequences that can be employed in the methods of this invention are well known in the art and thus one of skill in the art would be able to readily produce any number of additional siRNA sequences based on the known nucleotide sequence for HDAC4 and test each such sequence for activity as a silencing RNA of HDAC4, according to standard methods in the art. Thus, the present invention includes any siRNA of HDAC4, the production and characterization of which is well within the skill of the ordinary artisan.

In another embodiment, the present invention provides a method of modulating muscle remodeling signaling in a cell, comprising contacting the cell with an inhibitor of HDAC4 activity. As used herein, the term "modulating" means to regulate, adjust, and/or alter cell signaling pathways involved in muscle remodeling (Bassel-Duby and Olson, "Signaling Pathways in Skeletal Muscle Remodeling, Annual Review of Biochemistry" 75:19-37 (2006).

In a further embodiment, the present invention provides a method of increasing peroxisome proliferator-activated receptor-γ coactivator (PGC)-1α expression in a cell, comprising contacting the cell with an inhibitor of HDAC4 activity. In some embodiments, the present invention provides a method to improve insulin responsiveness in a subject, comprising increasing peroxisome proliferator-activated receptor-γ coactivator (PGC)-1α expression in a cell by contacting the cell with an inhibitor of HDAC4 activity. In some embodiments, the present invention provides a method to reduce susceptibility to muscular atrophy in a subject, comprising increasing peroxisome proliferator-activated receptor-γ coactivator (PGC)-1α expression in a cell by contacting the cell with an inhibitor of HDAC4 activity. As used herein, expression refers to the process by which the DNA sequence of a gene or coding sequence is converted (e.g., transcribed and/or translated) into a functional protein or gene product. Further, as used herein, increasing or decreasing expression refers to an increase or decrease, respectively, in the amount of protein expressed (i.e., produced) from the transcription and/or translation of a gene or coding sequence.

In another embodiment, the present invention provides a method of decreasing muscle-specific RING finger protein 1 (MuRF1) expression in a cell, comprising contacting the cell with an inhibitor of HDAC4 activity. In some embodiments, the present invention provides a method to prevent muscular atrophy in a subject, said method comprising decreasing muscle-specific RING finger protein 1 (MuRF1) expression in a cell by contacting the cell with an inhibitor of HDAC4 activity.

In an additional embodiment, the present invention provides a method of increasing Dachschund 2 (Dach 2) activity in a cell, comprising contacting the cell with an inhibitor of HDAC4 activity. In some embodiments, the present invention includes a method of increasing slow/oxidative fiber formation in a subject, comprising increasing Dachschund 2 (Dach 2) activity in a cell by contacting the cell with an inhibitor of HDAC4 activity.

In a further embodiment, the present invention provides a method of decreasing myogenin activity in a cell, comprising contacting the cell with an inhibitor of HDAC4 activity.

In another embodiment, the present invention provides a method of decreasing nicotinic acetylcholine receptor (nAChR) alpha, beta, and/or gamma subunit expression in a muscle cell, comprising contacting the cell with an inhibitor of HDAC4 activity.

In another embodiment, the present invention provides a method of treating muscular atrophy in a subject, comprising administering to the subject an effective amount of an inhibitor of HDAC4 activity.

In another embodiment, the present invention provides a method of treating diabetes in a subject, comprising administering to the subject an effective amount of an inhibitor of HDAC4 activity. As used herein, diabetes or diabetes mellitus refers to a metabolic disorder (type 1, type 2, and gestational diabetes) characterized by hyperglycemia (high blood sugar) and other signs, as distinct from a single illness or condition.

In another embodiment, the present invention provides a method of treating insulin resistance in a subject, comprising administering to the subject an effective amount of an inhibitor of HDAC4 activity. As used herein, insulin resistance refers to a condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

In another embodiment, the present invention provides a method of increasing insulin sensitivity in a subject, comprising administering to the subject an effective amount of an inhibitor of HDAC4 activity.

The present invention further provides a method of treating muscular atrophy associated with HDAC4 in a subject, comprising administering to the subject an effective amount of an inhibitor of HDAC4 activity.

The present invention further provides screening methods for identifying a substance as a modulator of HDAC4 activity. Thus, in some embodiments, the present invention provides a method of identifying a substance as an inhibitor of HDAC4 activity comprising; a) contacting the substance with HDAC4 and a substrate that is deacetylated by HDAC4 (e.g., histones, MEF2 proteins), under conditions whereby the deacetylation activity of HDAC4 can occur and measuring the amount of deacetylation of the substrate by HDAC4 in the presence of the substance (e.g., HDAC4 deacetylation can be assayed by using an in vitro deacetylation reaction consisting of recombinantly produced HDAC4 protein, $^{14}$C-labeled acetylated histones or MEF-2, and reaction buffer. The amount of deacetylation can be detected by quantitating the amount of carbon-14 produced as a by-product of the deacetylation reaction using a scintillation counter to measure radioactivity.); b) measuring the amount of deacetylation of the substrate in the absence of the substance; and c) comparing the amount of deacetylation of the substrate of step (a) and step (b), whereby a decrease in the amount of deactylation of the substrate of step (a) identifies a substance as an inhibitor of HDAC4 activity.

"Treat," "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay in the progression of the condition, prevention or delay of the onset of the disorder, and/or change in clinical parameters, disease or illness, etc., as would be well known in the art.

As used herein, "effective amount" refers to an amount of a compound or composition of this invention that is sufficient to produce a desired effect, which can be a therapeutic effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000)).

The present invention further provides a composition (e.g., a pharmaceutical composition) comprising an inhibitor of HDAC4 activity, either alone (e.g., as a single HDAC4 inhibitor or as a single composition of one or more HDAC4 inhibitors) and/or in any combination with one or more therapeutic reagents of this invention (e.g., a chemotherapeutic drug, an Hsp90 inhibitor, etc.), and these compositions can be present in a pharmaceutically acceptable carrier. The compositions described herein can be formulated for administration in a pharmaceutical carrier in accordance with known techniques. See, e.g., Remington, *The Science And Practice of Pharmacy* (latest edition). By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of this invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients.

A "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include, without limitation, any of the standard pharmaceutical carriers such as phosphate buffered saline solutions, water, emulsions such as oil/water emulsion, microemulsions and various types of wetting agents.

The pharmaceutical compositions of this invention include those suitable for administration to subjects in need thereof. As used herein, administer or administration refers to oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered.

Pharmaceutical compositions suitable for oral administration can be presented in discrete units, such as capsules, cachets, lozenges, or tables, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a composition of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sub-lingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions of this invention suitable for parenteral administration can comprise sterile aqueous and non-aqueous injection solutions of the composition of this invention, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit\dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 0.1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration are preferably presented as unit dose suppositories. These can be prepared by admixing the composition with one or more conventional solid carriers, such as for example, cocoa butter and then shaping the resulting mixture.

Pharmaceutical compositions of this invention suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharmaceutical Research* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

An effective amount of a composition of this invention, the use of which is in the scope of present invention, will vary from composition to composition, and subject to subject, and will depend upon a variety of well known factors such as the age and condition of the patient and the form of the composition and route of delivery. An effective amount can be determined in accordance with routine pharmacological procedures known to those skilled in the art. As a general proposition, a dosage from about 0.1 µg/kg to about 50 mg/kg will have therapeutic efficacy, with all weights being calculated based upon the weight of the composition.

The frequency of administration of a composition of this invention can be as frequent as necessary to impart the desired therapeutic effect. For example, the composition can be administered one, two, three, four or more times per day, one, two, three, four or more times a week, one, two, three, four or more times a month, one, two, three or four times a year or as necessary to control the condition. In some embodiments, one, two, three or four doses over the lifetime of a subject can be adequate to achieve the desired therapeutic effect. The amount and frequency of administration of the composition of this invention will vary depending on the particular condition being treated or to be prevented and the desired therapeutic effect.

The compositions of this invention can be administered to a cell of a subject either in vivo or ex vivo. For administration to a cell of the subject in vivo, as well as for administration to the subject, the compositions of this invention can be administered, for example as noted above, orally, parenterally (e.g., intravenously), by intramuscular injection, intradermally (e.g., by gene gun), by intraperitoneal injection, subcutaneous injection, transdermally, extracorporeally, topically or the like.

If ex vivo methods are employed, cells or tissues can be removed and maintained outside the body according to standard protocols well known in the art while the compositions of this invention are introduced into the cells or tissues. For example, a nucleic acid of this invention can be introduced into cells via any gene transfer mechanism, such as, for example, virus-mediated gene delivery, calcium phosphate mediated gene delivery, electroporation, microinjection and/or proteoliposomes. The transduced cells can then be infused (e.g., in a pharmaceutically acceptable carrier) or transplanted back into the subject per standard methods for the cell or tissue type. Standard methods are known for transplantation or infusion of various cells into a subject.

The present invention is more particularly described in the Examples set forth below, which are not intended to be limiting of the embodiments of this invention.

EXAMPLES

Example I

HDAC4 Connects Neural Activity to Muscle Transcriptional Reprogramming

Plasmids. HDAC4wt and HDAC4-3SA DNA fragments containing 5' EcoRI and 3' SmaI sites were cloned into the RI/SmaI site on the vector GFP expressing plasmid, pEGFP-C1, to generate N-terminal GFP tagged HDAC4wt and HDAC4-3SA mutant used in the electroporation experiments described in the section below entitled "HDAC4 is required for proper activity-dependent Dach2, MGN and nAChR gene expression."

Mouse Procedures. Mice were anaesthetized with a Ketamine/Xylazine mixture (25 mg/ml Ketamine, 1 mg/ml Xylazine in 0.9% NaCl; 100 ul used per mouse. Hair was removed from area surrounding muscle. For denervation, sciatic nerve was exposed and ~5 mM piece of nerve was cut and removed. Incision was sutured and mice were allowed to recover. For overexpression electroporation analysis, 25 ug GFP, HDAC4-GFP, or HDAC4-3SA-GFP was used for injection. For siRNA experiments, 500 pmol siRNA oligo was used for injection. DNA or siRNA were directly injected into TA muscles using cemented MicroSyringe (VWR). ECM 830 electroporator (BTX) was used for all electroporations. Tweezertrodes (Model 520) were coated with transmission gel and were placed outside the skin around the muscle belly and pulsed 5 times at 50V, 60 ms duration, with 200 ms interval time. Mice were allowed to recover in their cages. Stealth siRNA duplexed oligos are from Invitrogen. Sequences are; mouse HDAC4: 5' CACCGGAACCUGAACCACUGCAUUU 3' (SEQ ID NO:3), mouse HDAC5: 5' GGUCCUCAUCGUG-GACUGGGAUAUU 3' (SEQ ID NO:4).

Western Analysis. Tibialis muscles were isolated and frozen in liquid nitrogen. Muscles were dounce homogenized on ice using 1 ml glass-on-glass homogenizers and grinded in RIPA buffer (0.05M NaCl, 0.02M Tris, pH 7.6, 1 mM EDTA, supplemented with Leupeptin, Aprotinin, PMSF, NaF, sodium orthovanadate, and 1 mM DTT). Lysates were incubated with 1× detergent (1% NP-40, 0.5% sodium deoxycholate, 0.1% SDS) for 10 min rocking at 4° C. and centrifuged at 14000 rpm for 10 min to pellet debris. Protein was quantitated using Bradford assay (Biorad). The HDAC4 polyclonal antibody ab186 was used as described previously (35). Monoclonal α-tubulin (Sigma) and histone H3 (Upstate) antibodies were diluted 1:1000. For HDAC4 westerns, 50 ug protein lysate was used and HDAC4 antibody was diluted 1:300. Fractionation of muscle tissue was performed according to Siu et al. (36).

RNA analysis. For RNA analysis, TA muscles were dounce homogenized in 1 ml Tri reagent (MRC) and incubated at 4° C. overnight. 200 ul chloroform was added, and after vigorous shaking, samples were centrifuged at 12000 rpm for 10 min. Top aqueous layer was added to 500 ul isopropanol, mixed well, and centrifuged at 12000 rpm for 10 min. RNA pellet was washed with 70% ethanol, air-dried, and resuspended in DEPC water for RT-PCR analysis. For northern blotting, 10 ug total RNA was run on a 1% formaldehyde RNA gel. Gel was transferred onto Hybond N+ membrane and probed using radiolabeled fragments of HDAC4 or Atrogin-1 cDNA generated from Prime-it kit II (Stratagene). Blots were exposed for 2 hr at −80° C. For RT-PCR analysis, total RNA was DNase treated using DNA-free kit (Ambion), and 1 ug RNA was used for cDNA synthesis reaction using iScript cDNA Synthesis Kit (Biorad). Samples were diluted 1:50 and 5 ul cDNA was used per RT-PCR reaction. Real-time quantitative PCR was performed using iQ SYBER Green Supermix on the iCycler™ iQ Detection System (Biorad). Sample volume was 20 ul per reaction. Efficiency and specificity of primers were confirmed by standard PCR and DNA electrophoresis. RT-PCR Program on iCycler™ was 95° C. 15 sec, 60° C. 30 sec, 72° C. 30 sec. All real-time PCR values were normalized to either actin or 18S rRNA. RT-PCR primer sequences are as follows: G-actin: forward 5'-ACCCAG-GCATTGCTGACAGGATGC 3' (SEQ ID NO:5), reverse 5' CCATCTAGAAGCATTTGCGGTGGACG 3' (SEQ ID NO:6); 18S: forward 5' GGACCAGAGCGAAAGCATTT 3' (SEQ ID NO:7), reverse 5' TGCCAGAGTCTCGTTCGT-TAT 3' (SEQ ID NO:8); Dach2: forward 5'-ACTGAAAGTG-GCTTTGGATAA 3' (SEQ ID NO:9), reverse 5' TTCA-GACGCTTTTGCATTGTA 3' (SEQ ID NO:10); nAChRα: forward 5' CGTCTGGTGGCAAAGCT 3' (SEQ ID NO:11), reverse 5'-CCGCTCTCCATGAAGTT 3' (SEQ ID NO:12); MGN: forward 5'-CTCAGCTTAGCACCGGAAGCCCGA 3' (SEQ ID NO:13, reverse 5' ATTGCCCCACTCCG-GAGCGCAGGAG 3' (SEQ ID NO:14); MUSK: forward 5' CTCGTCCTCCCATTAATGTAAAAA 3' (SEQ ID NO: 15), reverse 5' TCCAGCTTCACCAGTTTGGAGTAA 3' (SEQ ID NO:16); HDAC4: forward 5' CAGATGGACTTTCTG-GCCG 3' (SEQ ID NO: 17), reverse 5' CTTGAGCTGCTG-CAGCTTC 3' (SEQ ID NO:18); HDAC5: forward 5' GAAG-CACCTCAAGCAGCAGCAGG 3' (SEQ ID NO:19, reverse 5' CACTCTCTTTGCTCTTCTCCTTGTT 3' (SEQ ID NO:20); HDAC7: forward 5' AGCTGGCTGAAGTGATCC 3' (SEQ ID NO:21), reverse 5' TCACCATCAGCCTCTGAG 3' (SEQ ID NO:22); HDAC9 (MITR): forward 5' TCAGAG-GTTCCTATGGGCCTG 3' (SEQ ID NO:23); reverse 5' TGGAGACGTTCCACTGAGGG 3' (SEQ ID NO:24).

Immunohistochemistry. Mouse muscle tissues were excised and placed in trays containing OCT Compound (VWR). Either longitudinal or cross-sections were prepared using a Cryostat at 4° C. Sections were kept at −80° C. until use. For immunostaining, sections were fixed for 10 min in 4% paraformaldehyde at room temperature. After washing in PBS 3×5 min, sections were blocked in 5% goat serum for 2 hr and then incubated overnight with primary antibodies. Primary antibody dilutions are as follows: HDAC4 (clone 186) 1:200, P467-HDAC4 (clone 19111)1:100, 14-3-3 (K-19, Santa Cruz) 1:100, CAMKIIδ (A-17, Santa Cruz). Sections were washed in PBS 3×5 min, blocked 90 min in goat serum, and incubated in secondary antibody for 2 hr, either with or without bungarotoxin as indicated. Secondary antibodies used were from Jackson ImmunoResearch (West Grove, Pa.) and included goat anti-rabbit RedX, goat anti-mouse Cy3, and goat anti-mouse Cy2. Bungarotoxin-labeled FITC or Rhodamine was used (Molecular Probes). Sections were immersed in mounting medium (fluoromount G. Southern Biotech) for visualization. All images shown were taken with a Zeiss Axioskop compound microscope with a 4×, 20× or 40× objective.

Skeletal muscle HDAC4 expression is dramatically induced in response to denervation and neuromuscular defects associated with diseases. As immobilization causes reduction in neuromuscular activity, it was investigated whether HDAC4 is regulated by neural activity in skeletal muscle. To test this, a mouse denervation model of inactivity was employed. Adult mice were right-limb denervated for 7 days and gastrocnemius muscles were subjected to western analysis with an HDAC4 specific antibody and it was shown that HDAC4 protein was dramatically increased in denervated muscle compared to the contralateral control muscles. The induction of HDAC4 occurs within 24 hours after denervation and appears to be maximal by 7 days post-denervation. These results demonstrate that HDAC4 expression is rapidly and robustly induced in response to denervation.

The induction of HDAC4 in response to denervation could occur at the level of protein stability or at the level of transcriptional regulation. To distinguish between these two possibilities, RNA was analyzed by northern blot and quantitative real-time RT-PCR from both control and denervated tibialis muscle samples. Northern blotting analysis showed that denervation induced a dramatic induction of the HDAC4 transcript, confirming a transcriptional mode of regulation on HDAC4. Real-time PCR analysis demonstrated that HDAC4 RNA levels are induced by more than ten-fold. Interestingly, HDAC5 was also markedly induced by denervation, while HDAC7 and HDAC9 levels are either not effected or modestly reduced. These data indicate that HDACs 4 and 5 may be a part of a muscle transcriptional program in response to inactivity.

Reduced neural activity caused by denervation is a common hallmark of neuromuscular disease. To assess whether HDAC4 is also involved in skeletal muscle abnormality associated with neuromuscular disease, HDAC4 levels in amyotrophic lateral sclerosis (ALS) mice (SOD1-G93A) and NMD mice (spinal muscular atrophy (SMARD1) model) were examined. HDAC4 is dramatically induced in skeletal muscle from both ALS and NMD (neuromuscular degeneration model) mice, which represent two neurogenic models with significant neuromuscular defects.

Interestingly, at ~day 120 when there was no discernible motor defect, HDAC4 was selectively induced in tibialis anterior (TA) muscle, a fast/glycolytic fiber, but not in the soleus, which is predominantly slow/oxidative fibers. This finding is in agreement with the observation that fast fibers in ALS mice develop atrophy before slow fibers, further connecting HDAC4 induction to neuromuscular dysfunction. In contrast, DMD (Duchenne Muscular Dystrophy caused by dystrophin mutation) and LGMD (Limb-Girdle Muscular Dystrophy caused by myotilin mutation) models, which display myogenic muscular dystrophies in the absence of neuromuscular defects, showed no significant elevation of HDAC4 levels. Therefore, HDAC4 is specifically induced in response to neural inactivity as opposed to muscle dysfunction.

HDAC4 is present at the NMJ and its subcellular localization is regulated by innervation. Class IIA HDACs have been shown to dynamically shuttle between the nucleus and the cytoplasm, so the subcellular localization of HDAC4 in response to denervation was investigated. Gastrocnemius muscle sections were prepared from control and denervated muscle, and immunohistochemistry was performed using a specific HDAC4 antibody. Control muscles display some sarcoplasmic staining with weak nuclear staining, indicating a basal level of nuclear HDAC4 under normal conditions. However, 7-day denervated samples displayed a dramatic nuclear accumulation of HDAC4, indicating a re-localization of HDAC4 to the nucleus during inactivity. Biochemical fractionation of denervated muscle similarly revealed a marked increase in nuclear HDAC4 levels by 2 days post-denervation, consistent with a denervation-dependent nuclear entry for HDAC4. The above results indicate that HDAC4 is responsive to changes in neural activity.

During the characterization of HDAC4 subcellular localization in myofibers, large structures that stained positive for HDAC4 were consistently observed. Co-staining with α-bungarotoxin, which binds nAChRα, demonstrated that those structures are neuromuscular junctions (NMJ). Moreover, using a phospho-specific antibody that recognizes HDAC4 phosphorylated on serine 467, a preferred CaMKII site, abundant phosphorylated HDAC4-S467 staining at the NMJ was detected. As HDAC4 can be regulated by CaMKII phosphorylation and 14-3-3 binding, the localization of CaMKII and 14-3-3 was investigated using specific antibodies. CAMKIIδ and 14-3-3 were also found concentrated at the NMJ, indicating that HDAC4 and its regulators are all localized to the NMJ. To determine if HDAC4 localization to the NMJ is regulated in response to altered neural activity, denervated muscle sections were analyzed with HDAC4 antibodies. Denervation induced a rapid dissociation of HDAC4 from the NMJ, while CaMKII and 14-3-3 localization to the NMJ remained largely unchanged. These results indicate that HDAC4 and its associated machinery are all components of the NMJ and indicate that HDAC4 may be regulated by neural activity locally at NMJ.

HDAC4 is required for proper activity-dependent Dach2, MGN and nAChR gene expression. The above results revealed that HDAC4 expression is induced and undergoes nuclear translocation upon denervation, suggesting a role for HDAC4 in an activity-dependent transcriptional re-programming in skeletal muscle. Next, studies were conducted to determine the identify genes regulated by HDAC4 in response to denervation. First, the kinetics of HDAC4 induction in relation to the Dach2, MGN, and nAChR gene expression were determined, thereby establishing a temporal relationship of this transcription network in response to denervation. To this end, mice were denervated and tibialis muscles were harvested at varying time points for RNA analysis. Real time PCR analysis detected abundant HDAC4 levels by 12 hours post-denervation, at time at which Dach2 levels begin to decline. Subsequently, MGN and nAChR levels begin to accumulate around 24 hours post-denervation. This analysis revealed that the induction of HDAC4 coincides with the repression of Dach2, and that this temporal regulation may represent an early event required for the subsequent induction of myogenin-dependent target genes, including nAChR.

Second, it was determined whether HDAC4 regulates Dach2 expression. To this end, wild-type HDAC4 as well as the constitutively nuclear mutant, HDAC4-3SA, were electroporated into mouse tibialis muscle and RNA samples were prepared and analyzed by RT-PCR. Both HDAC4-wt and the HDAC4-3SA mutant were capable of repressing Dach2 levels in this system, although Dach2 was more potently repressed by HDAC4-3SA, consistent with this mutant being constitutively nuclear. Both wild-type HDAC4 and HDAC4-3SA expression led to moderate induction of activity-dependent signaling as MGN and nAChR mRNA were elevated compared to GFP-alone electroporated fibers. These data indicate that HDAC4-mediated repression of Dach2 is sufficient to activate activity-dependent gene expression leading to nAChR induction.

Third, to further evaluate the role of HDAC4 in activity-dependent Dach2-MGN-nAChR transcriptional cascade, an in vivo knockdown approach was employed using stealth siRNA technology (Invitrogen). A scrambled control siRNA or an HDAC4 siRNA duplex was electroporated into mouse tibialis muscle, and 7 days after electroporation mice were denervated for 3 days for subsequent muscle analysis by RT-PCR. Dach2 levels are reduced during denervation with a concomitant induction of both MGN and nAChR levels. siRNA-mediated knock-down of HDAC4 significantly alleviates the repression of Dach2 that occurs during denervation. Supporting this observation, HDAC4 siRNA also dramatically reduced the induction of both MGN and nAChR after denervation. Double knockdown of HDAC4 and HDAC5 shows a similar phenotype to that of the HDAC4 single knockdown, revealing the dominant role of HDAC4 in this regulation. These data support the idea that HDAC4 is required for activity-dependent induction of nAChR expression, and that HDAC4 mediates this effect through repression of Dach2.

HDAC4 regulates nAChR distribution. Studies were conducted to examine the distribution of nAChR in myofibers electroporated with HDAC4-wt and HDAC4-3SA. Muscle fibers expressing either wild-type HDAC4 or HDAC4-3SA mutant consistently displayed a broad distribution of nAChR along the surface of the fiber as determined by bungarotoxin staining, indicative of extrasynaptic expression of nAChR caused by elevated nAChR expression. Furthermore, in myofibers over-expressing HDAC4, prominent intracellular accumulation of nAChR was observed, suggesting abnormal nAChR distribution. Importantly, similar abnormal nAChR distribution and structures were observed in atrophic muscles from SOD-1 transgenic mice, supporting the idea that elevated HDAC4 levels can lead to abnormal nAChR distribution. These data reveal that HDAC4 mediated regulation of Dach2/MGN/nAChR regulates expression and localization of nAChR.

Example II

HDAC4 is Required for the Proper Execution of Muscle Atrophy Program Activated by Surgical Denervation To establish a role for HDAC4 in muscle atrophy, scrambled control siRNA or HDAC4-specific siRNA were electroporated into tibialis anterior (TA) followed by denervation. HDAC4 siRNA results in more than 80% reduction in HDAC4. An expression plasmid for GFP was co-electroporated to mark the transfected fibers. The extent of muscle atrophy was then analyzed by measuring muscle fiber size and the induction of atrophy-specific genes, MuRF1 and atrogin 1, two E3 ligases essential for muscle atrophy. As expected, TA muscle that received control siRNA undergoes prominent reduction in size after denervation for 12 days. This atrophy is largely prevented in TA electroporated with the HDAC4 siRNA. Direct measurement of individual fibers of denervated muscles demonstrates that muscle fibers that received HDAC4 siRNA are much larger than those that received control siRNA. These results provide the first experimental evidence that HDAC4 is required for proper execution of muscle atrophy caused by surgical denervation. Supporting this conclusion, upon examining the expression of MuRF1 and atrogin-1 by RT-PCR, the induction of MuRF1 by denervation was found to be significantly inhibited in muscles expressing HDAC4 siRNA while atrogin 1 expression is modestly affected. Thus, inactivation of HDAC4 spares muscle from atrophy and the induction of MRF1 by surgical denervation. These findings strongly indicate that pharmacological inhibition of HDAC4 can be an effective therapeutic intervention for muscle atrophy caused by neuromuscular disease and inactivity.

Example III

Differential HDAC4 Phosphorylation and Subcellular Localization is Regulated by Neural Activity and is Critical for Regulating MEF2 Activity in Fiber Type Specification and Remodeling Fiber type-specific and neural activity-dependent distribution and phosphorylation of HDAC4. Immuno-staining studies were performed to localize HDAC4 in normal and denervated muscle. In control gastrocnemius-soleus muscle, a distinct HDAC4 staining pattern in slow vs. fast fiber was observed. HDAC4 was found localized to the nucleus in fast fiber-enriched gastrocnemius. In contrast, prominent cytosolic staining for HDAC4 was clearly observed in slow fiber-enriched soleus. This differential localization indicates that HDAC4 might be differentially regulated in slow/oxidative vs. fast/glycolytic fibers. Thus, HDAC4 is differentially localized in fast and slow fibers and is concentrated to nuclei in denervated muscle.

Supporting this hypothesis, Western blot analysis shows that HDAC4 produced in white vastus (WV) and tibialis (TA), which consist of mostly fast fiber, migrates consistently faster than HDAC4 from slow-fiber enriched soleus. This mobility difference disappears after phosphatase treatment, suggesting differential phosphorylation of HDAC4 in two different fiber types. Indeed, using an antibody that specifically recognizes HDAC4 phosphorylated at S467, it was determined by Western blot analysis that HDAC4 in soleus is hyper-phosphorylated compared to that in TA or WV muscle.

Further, muscle from transgenic mice expressing a MCK-driven, constitutively activated calcineurin was analyzed. This transgene induces slow/oxidative fiber formation in normally fast/glycolytic fiber-dominant TA and WV. HDAC4-S467 phosphorylation was indeed markedly induced in TA and WV muscle from the calcineurin-transgenic mouse, correlating HDAC4 hyper-phosphorylation with an induction of slow/oxidative fibers. In control mouse, HDAC4-S467 phosphorylation is high in soleus and low in TA and WV as expected. Thus, HDAC4 is differentially distributed and phosphorylated in slow/oxidative vs. fast/glycolytic fibers. Upon denervation, the intensity of HDAC4 staining increases dramatically and HDAC4 becomes accumulated in the nucleus in all fibers examined.

Of significance, the hyper-phosphorylation and more cytosolic localization of HDAC4 in slow/oxidative fibers correlate well with the observation that MEF2 activity is more active in the slow/oxidative fibers. Further, the nuclear accumulation of HDAC4 in slow/oxidative fiber is consistent with the loss of MEF2 activity after denervation. Thus, HDAC4 causes an increase in PGC1-α and markers for oxidative fibers in muscle. These findings indicate that differential HDAC4 phosphorylation and subcellular localization is regulated by neural activity and critical for regulating MEF2 activity in fiber type specification and remodeling.

Inactivation of HDAC4 by siRNA or inhibitor TSA induces PGC-1α expression in skeletal muscle. To investigate whether HDAC4 regulates PGC-1α expression and fiber type specification, HDAC4-siRNA was electroporated into fast/glycolytic tibialis anterior muscle. Inactivation of HDAC4 results in an elevation of PGC-1α expression and myoglobin expression, a key marker for oxidative/slow fibers. These findings indicate that HDAC4 suppresses slow/oxidative fiber type via the inhibition of PGC-1α. Further supporting this conclusion, daily injection of a HDAC inhibitor Trichostatin A can also increase the level of PGC-1α.

Example IV

HDAC4 and HDAC5 Regulate Pro-Inflammatory Cytokines

The induction of proinflammatory cytokines, such as TNFα, IL1 and IL6, appears to be associated with various chronic disease conditions, including cancer cachexia. Some of these cytokines induce the E3 ligase, MURF1, crucial for muscle atrophy. In cancer patients, cachexia has been estimated to contribute up to a third of all deaths. These findings underscore the critical importance of uncovering the regulatory mechanism that controls pro-inflammatory cytokine induction in muscle atrophy, as it can provide a novel and efficient therapeutic intervention for muscle atrophy associated with various pathological conditions.

An investigation of inflammation-related gene expression in denervated muscle demonstrated a marked induction of proinflammatory cytokines, such as TNF□, IL1 and IL6. Importantly, this induction is blunted in denervated muscle that has been electroporated with siRNA for HDAC4 and HDAC5. Furthermore, in HDAC4 and HDAC5 siRNA transfected muscle, the expression of the AP1 transcription factor, c-jun and c-fos, which plays a key role in inducing proinflammatory gene expression, is also inhibited. Thus, inhibition of HDAC4 and HDAC5 suppresses AP1 activity and the induction proinflammatory cytokines. These results have several important implications: 1) The induction of proinflammatory cytokines could be a key to muscle atrophy caused by denervation and neuromuscular disease. 2) The induction of proinflammatory cytokines in denervated muscles requires HDAC4 and/or HDAC5. 3) The protective effect of inhibition of HDAC4 and/or HDAC5 against denervation-induced muscle atrophy demonstrates that HDAC4 and/or HDAC5 are required for proinflammatory cytokine induction, which in turn promotes muscle atrophy. 4) Pharmacological inhibition of HDAC4 and HDAC5 could suppress proinflammatory cytokine induction, thereby alleviating muscle atrophy caused by neuromuscular disease. 5) Given the critical importance of proinflammatory cytokine induction in cachexia, pharmacological inhibition of HDAC4 and HDAC5 could also alleviate cachexia including that associated with cancer. Thus, pharmacological inhibitors of HDAC4 and/or HDAC5 could be potent anti-inflammatory agents.

A real-time RT-PCR superarray was used to determine whether inflammatory gene expression is regulated by class IIA HDACs 4/5. RNA from control denervated and HDAC4/5 siRNA electroporated denervated muscles was analyzed for expression of ~90 key inflammatory genes and plotted as fold induction as shown in FIG. 1A. Significantly, many inflammatory genes, which are induced during denervation atrophy, are suppressed in the absence of HDAC4/5. Some prominent examples, including IL-1α, IL-1β, IL-2, IL-6, and TNFα are shown. It was also observed that c-fos and C-jun levels are also down-modulated in HDAC4/5 deficient muscle fibers (FIG. 1B). To confirm these findings, levels of IL-1β and IL-6 were measured in control and HDAC4/5 siRNA muscles in two control-denervated and two HDAC4/5 siRNA transfected denervated muscles by real time PCR (FIG. 1B). Denervation induces IL-1β and IL-6 and this induction is abrogated in HDAC4/5 siRNA transfected muscle.

An expression plasmid for either HDAC4-activated c-fos promoter-driven or HDAC4 activated c-jun promoter driven luciferase reporter gene expression was transfected into NIH3T3 cells. HDAC4 activated c-fos promoter driven luciferase expression was increased ~4 fold and HDAC activated c-jun promoter driven luciferase expression was increased ~8 fold (FIG. 1C). HDAC4 activation of c-jun transcription was dependent on the AP-1 site but not on the MEF2 binding site present in the c-jun promoter, as a mutation of the AP-1 site, but not the MEF2 site significantly reduced HDAC4-mediated activation of c-jun transcription.

In further studies, either wild type HDAC4 or an enzymatically inactive HDAC4 mutant, H803A, were transfected with the c-jun promoter into NIH3T3 cells. As shown in FIG. 1D, only wild type HDAC4, but not the H803A mutant HDAC4 efficiently activated c-jun transcription.

Example V

HDAC4 and HDAC5 Regulate PGC1α Expression Controlled by Neural Activity

Denervation and reduced activity promote oxidative fiber transition into more glycolytic fibers, at least in part, by repressing the transcription co-activator PGC 1α. The transition into more glycolytic fibers is associated with insulin resistance and type II diabetes. Transcriptional repression of PGC1α by denervation is shown to be reversed by the electroporation of HDAC4 and HDAC5 siRNA. These results further suggest that pharmacological inhibition of HDAC4 and HDAC5 could provide additional therapeutic benefits by modulating the expression of PGC1α, which would promote more oxidative muscle fiber with enhanced insulin response and more resistance to atrophy. Supporting the conclusion that inactivation of HDAC4 and HDAC5 promotes more oxidative fibers, an induction of myoglobin and cytochrome C, two key components enriched in oxidative fibers, was observed in muscle expressing HDAC4 and HDAC5 siRNA.

Figure 2:
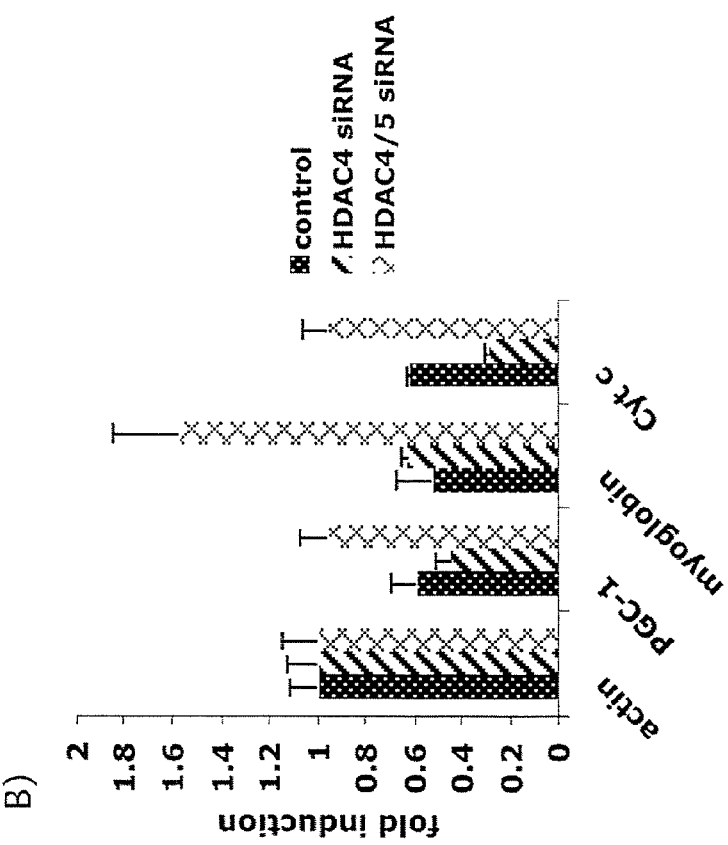
FIGS. 2A-B. The expression of PGC-1alpha and other metabolic genes was evaluated in HDAC4 over-expressing and HDAC siRNA denervated muscles by real time PCR analysis using metabolic gene specific primers. A. The levels of PGC-1 and myoglobin genes were reduced in muscles expressing wild type HDAC4 and in muscles containing a HDAC4-3SA nuclear mutant. B. Denervated muscles show a reduction in PGC-1, myoglobin and cytochrome c gene expression but denervated muscles lacking HDAC4+5 showed a dramatic rescue of these genes.
Figure 2:
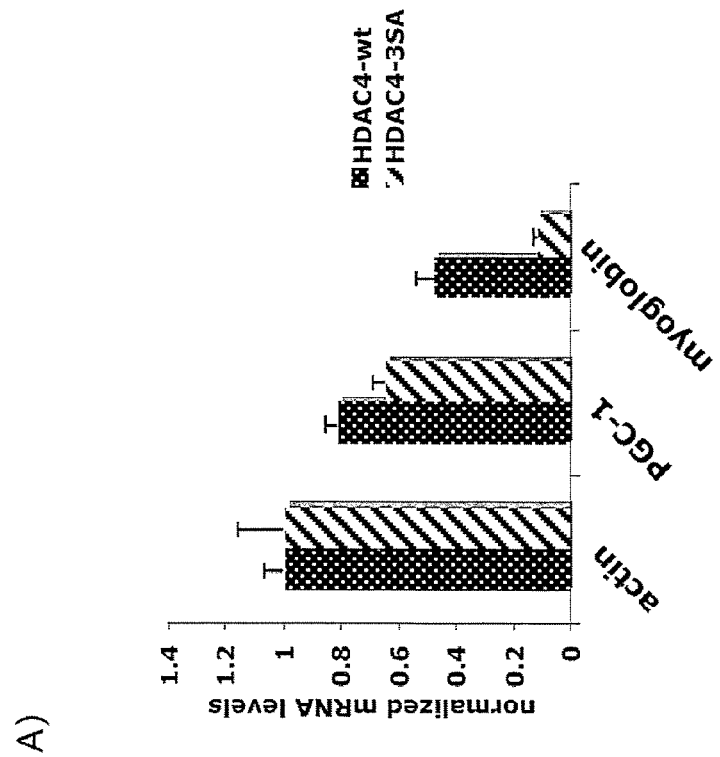

The expression of PGC-1alpha and additional metabolic genes were evaluated in control, HDAC4 over-expressing and HDAC siRNA denervated muscles by real-time RT-PCR analysis using metabolic gene-specific primers. As shown in FIG. 2A, the levels of all metabolic target genes tested were reduced in muscles expressing wild-type HDAC4 and more dramatically in muscles containing a HDAC4-3SA nuclear mutant. Similarly, denervated muscles showed a reduction in metabolic gene expression (FIG. 2B); however, denervated muscles lacking HDAC4+5 showed a dramatic rescue of these genes, indicating that HDAC4/5 controls activity-dependent regulation of metabolic gene expression.

Example VI

Abnormal Distribution of HDAC4 in Human ALS

To further establish a role of HDAC4 in neuromuscular disease, HDAC4 was assessed in muscle biopsies from human ALS patients. Similar to the mouse ALS model, HDAC4 levels are also elevated in human ALS muscle. Muscle biopsies were taken from deltoid muscles of patients who were overtly healthy or diagnosed with muscle disease as follows: Patient 1: control; Patient 2: myopathy; Patient 3: ALS non-progressive; Patient 4: myopathy; Patient 5: ALS severe, progressive; Patient 6: control; Patient 7: myopathy; Patient 8: ALS non-progressive; Patient 9: control; and Patient 10: ALS severe, progressive. Biopsied samples were prepared for both Western and immunohistochemistry analysis. Western analysis was performed using antibodies against HDAC4 and α-ACTN-2. Samples were sectioned and stained using 1) antibodies against HDAC4, 2) dystrophin to mark fibers, and 3) Hoechst dye to mark nuclei. Upon examination of the subcellular localization of HDAC4, a striking nuclear accumulation of HDAC4 was observed in muscle from an ALS patient but not in muscle from a control non-ALS individual. These results demonstrate that HDAC4 becomes induced and accumulates in nuclei of muscle affected by ALS, indicating the involvement of HDAC4 in the pathological muscle remodeling associated with neuromuscular disease.

The foregoing is illustrative of the present invention, and is not to be construed as limiting thereof. The invention is defined by the following claims, with equivalents of the claims to be included therein. All publications, patent applications, patents, patent publications, sequences (nucleotide sequences, single polymorphism nucleotides, amino acid sequences, etc.) identified in the GenBank® database or other sequence databases and any other references cited herein are incorporated by reference in their entireties for the teachings relevant to the sentence and/or paragraph in which the reference is presented.

REFERENCES

1. Sanes, J. R. & Lichtman, J. W. (1999) *Annu Rev Neurosci* 22, 389-442.
2. Sanes, J. R. & Lichtman, J. W. (2001) *Nat Rev Neurosci* 2, 791-805.
3. McMahan, U. J. (1990) *Cold Spring Harb Symp Quant Biol* 55, 407-18.
4. Banks, G. B., Fuhrer, C., Adams, M. E. & Froehner, S. C. (2003) *J Neurocytol* 32, 709-26.
5. Blake, D. J., Tinsley, J. M. & Davies, K. E. (1996) *Brain Pathol* 6, 37-47.
6. Grady, R. M., Zhou, H., Cunningham, J. M., Henry, M. D., Campbell, K. P. & Sanes, J. R. (2000) *Neuron* 25, 279-93.
7. Schaeffer, L., de Kerchove d'Exaerde, A. & Changeux, J. P. (2001) *Neuron* 31, 15-22.
8. Mejat, A., Ravel-Chapuis, A., Vandromme, M. & Schaeffer, L. (2003) *Ann N Y Acad Sci* 998, 53-65.
9. Adams, L. & Goldman, D. (1998) *J Neurobiol* 35, 245-57.
10. Huang, C. F. & Schmidt, J. (1994) *FEBS Lett* 338, 277-80.
11. Macpherson, P., Kostrominova, T., Tang, H. & Goldman, D. (2002) *J Biol Chem* 277, 15638-46.
12. Tang, H., Macpherson, P., Argetsinger, L. S., Cieslak, D., Suhr, S. T., Carter-Su, C. & Goldman, D. (2004) *Cell Signal* 16, 551-63.
13. Neville, C., Schmidt, M. & Schmidt, J. (1991) *Neuroreport* 2, 655-7.
14. Bessereau, J. L., Stratford-Perricaudet, L. D., Piette, J., Le Poupon, C. & Changeux, J. P. (1994) *Proc Natl Acad Sci USA* 91, 1304-8.
15. Merlie, J. P., Mudd, J., Cheng, T. C. & Olson, E. N. (1994) *J Biol Chem* 269, 2461-7.
16. Su, C. T., Huang, C. F. & Schmidt, J. (1995) *FEBS Lett* 366, 131-6.
17. Tang, J., Jo, S. A. & Burden, S. J. (1994) *Development* 120, 1799-804.
18. Walke, W., Xiao, G. & Goldman, D. (1996) *J Neurosci* 16, 3641-51.
19. Gundersen, K., Rabben, I., Klocke, B. J. & Merlie, J. P. (1995) *Mol Cell Biol* 15, 7127-34.
20. Tang, H. & Goldman, D. (2006) *Proc Natl Acad Sci USA* 103, 16977-82.
21. McKinsey, T. A., Zhang, C. L., Lu, J. & Olson, E. N. (2000) *Nature* 408, 106-11.
22. Lu, J., McKinsey, T. A., Nicol, R. L. & Olson, E. N. (2000) *Proc Natl Acad Sci USA* 97, 4070-5.
23. Zhao, X., Ito, A., Kane, C. D., Liao. T. S., Bolger, T. A., Lemrow, S. M., Means, A. R. & Yao, T. P. (2001) *J Biol Chem* 276, 35042-8.
24. Bassel-Duby, R. & Olson, E. N. (2006) *Annut Rev Biochem* 75, 19-37.
25. Wu, H., Kanatous, S. B., Thurmond, F. A., Gallardo, T., Isotani, E., Bassel-Duby, R. & Williams, R. S. (2002) *Science* 296, 349-52.
26. Backs, J., Song, K., Bezprozvannaya, S., Chang, S. & Olson, E. N. (2006) *J Clin Invest* 116, 1853-64.
27. McKinsey, T. A., Zhang, C. L. & Olson, E. N. (2001) *Mol Cell Biol* 21, 6312-21.
28. Bodine, S. C., Latres, E., Baumhueter, S., Lai, V. K., Nunez, L., Clarke, B. A., Poueymirou, W. T., Panaro, F. J., Na, E., Dharmarajan, K., Pan, Z. Q., Valenzuela, D. M., DeChiara, T. M., Stitt, T. N., Yancopoulos, G. D. & Glass, D. J. (2001) *Science* 294, 1704-8.
29. Mejat, A., Ramond, F., Bassel-Duby, R., Khochbin, S., Olson, E. N. & Schaeffer, L. (2005) *Nat Neurosci* 8, 313-21.
30. Cox, G. A., Mahaffey, C. L. & Frankel, W. N. (1998) *Neuron* 21, 1327-37.
31. Maddatu, T. P., Garvey, S. M., Schroeder, D. G., Hampton, T. G. & Cox, G. A. (2004) *Hum Mol Genet* 13, 1105-15.
32. Klarsfeld, A. & Changeux, J. P. (1985) *Proc Natl Acad Sci USA* 82, 4558-62.
33. Macpherson, P. C., Cieslak, D. & Goldman, D. (2006) *Mol Cell Neurosci* 31, 649-60.
34. Macpherson, P. C., Stihr, S. T. & Goldman, D. (2004) *J Cell Biochem* 91, 821-39.
35. Bolger, T. A. & Yao, T. P. (2005) *J Neurosci* 25, 9544-53.
36. Siu, P. M., Pistilli, E. E., Murlasits, Z. & Alway, S. E. (2006) *J Appl Physiol* 100, 907-16.

What is claimed is:

1. A method of increasing slow/oxidative fiber formation in skeletal muscle, comprising contacting skeletal muscle cells with an inhibitor of HDAC4 activity.

2. A method of decreasing nicotinic acetylcholine receptor (nAChR) alpha, beta, and/or gamma subunit expression in a muscle cell, comprising contacting the cell with an inhibitor of HDAC4 activity.

3. A method of treating muscular atrophy in a subject, comprising administering to the subject an effective amount of an inhibitor of HDAC4 activity.

4. The method of claim 3, wherein muscular atrophy is associated with a neurodegenerative disorder, a neuromuscular disorder, HIV infection, inactivity, ageing, cancer, denervation and any combination thereof.

5. The method of claim 3, wherein muscular atrophy is associated with amyotrophic lateral sclerosis.

6. The method of claim 3, wherein muscular atrophy is associated with spinal muscular atrophy.

7. The method of claim 3, wherein muscular atrophy is associated with respiratory distress type 1 (SMARD1).

8. A method of treating diabetes in a subject, comprising administering to the subject an effective amount of an inhibitor of HDAC4 activity.

9. The method of claim 1, wherein the inhibitor of HDAC4 activity is selected from the group consisting of hydroxamic acid based HDAC inhibitors, Suberoylanilide hydroxamic acid (SAHA), NVP-LAQ824, LBH589, Trichostatin A, Scriptaid, m-Carboxycinnamic acid bishydroxamic acid (CBHA), ABHA, Pyroxamide, Propenamides, Oxamfiatin, 6-(3-Chlorophenylureido)caproic hydroxamic acid (3-Cl-UCHA), A-161906, jnj16241199, tubacin, small interfering RNA (siRNA), short chain fatty acid HDAC inhibitors, butyrate, phenylbutyrate, valproate, hydroxamic acid, trichostatins, epoxyketone-containing cyclic tetrapeptides, HC-toxin, Chiamydocin, Diheteropeptide, WF-3161, Cyl-1. Cyl-2, non-epoxyketone-containing cyclic tetrapeptides. Apicidin, cyclic-hydroxamic-acid-containing peptides (CHAPS), benzamides, CI-994, trapoxin, deprudecin, organosulfur compounds, MS275, depsipeptide (FK228) and any combination thereof.

10. The method of claim 1, wherein the cell is in a subject.

11. The method of claim 3, wherein the subject is human.

12. The method of claim 10, wherein the subject is human.

13. A method of decreasing inflammatory cytokine activity in a cell, wherein the inflammatory cytokine is selected from the group consisting of TNF alpha, interleukin-1 alpha, interleukin-1 beta, interleukin-2, interleukin-6 and any combination thereof, comprising contacting the cell with an inhibitor of HDAC4 activity.

14. The method of claim 13, wherein the cell is in a subject.

15. A method of decreasing c-jun and/or c-fos expression in a cell, comprising contacting the cell with an inhibitor of HDAC4 activity.

16. The method of claim 15, wherein the cell is in a subject.

17. A method of reducing inflammation in a subject, comprising administering to the subject an effective amount of an inhibitor of HDAC4 activity.

18. The method of claim 17, wherein the subject is a human.

19. The method of claim 17, wherein the inhibitor of HDAC4 activity is selected from the group consisting of hydroxamic acid based HDAC inhibitors, Suberoylanilide hydroxamic acid (SAHA), NVP-LAQS24, LBH589, Trichostatin A, Scriptaid, m-Carboxycinnamic acid bishydroxamic acid (CBHA), ABHA, Pyroxamide, Propenamides, Oxamflatin, 6-(3-Chlorophenylureido)caproic bydroxarn ic acid (3-Cl-UCHA), A-161906, jnj16241199, tubacin, small interfering RNA (siRNA), short chain fatty acid HDAC inhibitors, butyrate, phenylbutyrate, vaiproate, hydroxamic acid, trichostatins, epoxyketone-containing cyclic tetrapeptides, HC-toxin, Chiamydocin, Diheteropeptide, WF-3161, Cyl-1, Cyl-2, non-epoxyketone-containing cyclic tetrapeptides, Apicidin, cyclic-hydroxamic-acid-containing peptides (CHAPS), benzamides, CI-994, trapoxin, deprudecin, organosulfur compounds, MS275, depsipeptide (FK228) and any combination thereof.

20. The method of claim 19, wherein the siRNA is selected from the group consisting of the nucleotide sequence: 5' AAACGGUGGAUGUGGCCACGG 3' (SEQ ID NO:1), the nucleotide sequence: 5' AAGGAGCUGCUGAAIJCCUGCC 3' (SEQ ID NO:2), the nucleotide sequence: 5' CACCG-GAACCUGAACCACUGCAUUU 3' (SEQ ID NO 3) and any combination thereof.

\* \* \* \* \*

UNITED STATES PATENT AND TRADEMARK OFFICE
CERTIFICATE OF CORRECTION

PATENT NO. : 7,737,175 B2  
APPLICATION NO. : 12/130394  
DATED : June 15, 2010  
INVENTOR(S) : Yao et al.

It is certified that error appears in the above-identified patent and that said Letters Patent is hereby corrected as shown below:

On Title Page:

(56) References Cited, Page 2, Other Publications, right column, line 42 "PCT Application": Please correct "DHAC10" to read -- HDAC10 --
    Page 2, Other Publications, right column, line 53 "Nakamura":
    Please correct "IFN-α" to read -- IFN-β --

In the Specification:

Column 16, Line 33: Please correct "NO:13," to read -- NO:13), --
    Line 39: Please correct "NO:19," to read -- NO:19), --

In the Claims:

Column 32, Claim 9, Line 38: Please correct "Oxamfiatin" to read -- Oxamflatin --
    Line 44: Please correct "Chiamydocin" to read -- Chlamydocin --
    and "Cyl-1." to read -- Cyl-1, --
    Line 45; Please correct "tetrapeptides." to read -- tetrapeptides, --

Column 33, Claim 19, Line 6: Please correct "NVP-LAQS24"
    to read -- NVP-LAQ824 --
    Line 9: Please correct "bydroxarn ic" to read -- hydroxamic --
    Line 12: Please correct "vaiproate" to read -- valproate --
    Line 14: Please correct "Chiamydocin" to read -- Chlamydocin --

Column 34, Claim 20, Line 9: Please correct "GAAIJCCUGCC"
    to read -- GAAUCCUGCC --

Signed and Sealed this

Thirtieth Day of November, 2010

David J. Kappos  
*Director of the United States Patent and Trademark Office*

SEQUENCE LISTING

<160> NUMBER OF SEQ ID NOS: 24

<210> SEQ ID NO 1
<211> LENGTH: 21
<212> TYPE: RNA
<213> ORGANISM: Artificial
<220> FEATURE:
<223> OTHER INFORMATION: siRNA sequence

<400> SEQUENCE: 1

-continued aaacggugga uguggccacg g                                21

<210> SEQ ID NO 2
<211> LENGTH: 21
<212> TYPE: RNA
<213> ORGANISM: Artificial
<220> FEATURE:
<223> OTHER INFORMATION: siRNA sequence

<400> SEQUENCE: 2
aaggagcugc ugaauccugc c                                21

<210> SEQ ID NO 3
<211> LENGTH: 25
<212> TYPE: RNA
<213> ORGANISM: Artificial
<220> FEATURE:
<223> OTHER INFORMATION: siRNA sequence

<400> SEQUENCE: 3
caccggaacc ugaaccacug cauuu                            25

<210> SEQ ID NO 4
<211> LENGTH: 25
<212> TYPE: RNA
<213> ORGANISM: Artificial
<220> FEATURE:
<223> OTHER INFORMATION: siRNA sequence

<400> SEQUENCE: 4
gguccucauc guggacuggg auauu                            25

<210> SEQ ID NO 5
<211> LENGTH: 24
<212> TYPE: DNA
<213> ORGANISM: Artificial
<220> FEATURE:
<223> OTHER INFORMATION: RT-PCR primer

<400> SEQUENCE: 5
acccaggcat tgctgacagg atgc                             24

<210> SEQ ID NO 6
<211> LENGTH: 26
<212> TYPE: DNA
<213> ORGANISM: Artificial
<220> FEATURE:
<223> OTHER INFORMATION: RT-PCR primer

<400> SEQUENCE: 6
ccatctagaa gcatttgcgg tggacg                           26

<210> SEQ ID NO 7
<211> LENGTH: 20
<212> TYPE: DNA
<213> ORGANISM: Artificial
<220> FEATURE:
<223> OTHER INFORMATION: RT-PCR primer

<400> SEQUENCE: 7
ggaccagagc gaaagcattt                                  20

<210> SEQ ID NO 8
<211> LENGTH: 21
<212> TYPE: DNA
<213> ORGANISM: Artificial

```
<220> FEATURE:
<223> OTHER INFORMATION: RT-PCR primer

<400> SEQUENCE: 8
tgccagagtc tcgttcgtta t                                              21

<210> SEQ ID NO 9
<211> LENGTH: 21
<212> TYPE: DNA
<213> ORGANISM: Artificial
<220> FEATURE:
<223> OTHER INFORMATION: RT-PCR primer

<400> SEQUENCE: 9
actgaaagtg gctttggata a                                              21

<210> SEQ ID NO 10
<211> LENGTH: 21
<212> TYPE: DNA
<213> ORGANISM: Artificial
<220> FEATURE:
<223> OTHER INFORMATION: RT-PCR primer

<400> SEQUENCE: 10
ttcagacgct tttgcattgt a                                              21

<210> SEQ ID NO 11
<211> LENGTH: 17
<212> TYPE: DNA
<213> ORGANISM: Artificial
<220> FEATURE:
<223> OTHER INFORMATION: RT-PCR primer

<400> SEQUENCE: 11
cgtctggtgg caaagct                                                   17

<210> SEQ ID NO 12
<211> LENGTH: 17
<212> TYPE: DNA
<213> ORGANISM: Artificial
<220> FEATURE:
<223> OTHER INFORMATION: RT-PCR primer

<400> SEQUENCE: 12
ccgctctcca tgaagtt                                                   17

<210> SEQ ID NO 13
<211> LENGTH: 24
<212> TYPE: DNA
<213> ORGANISM: Artificial
<220> FEATURE:
<223> OTHER INFORMATION: RT-PCR primer

<400> SEQUENCE: 13
ctcagcttag caccggaagc ccga                                           24

<210> SEQ ID NO 14
<211> LENGTH: 25
<212> TYPE: DNA
<213> ORGANISM: Artificial
<220> FEATURE:
<223> OTHER INFORMATION: RT-PCR primer

<400> SEQUENCE: 14
attgccccac tccggagcgc aggag                                          25
```

<210> SEQ ID NO 15
<211> LENGTH: 24
<212> TYPE: DNA
<213> ORGANISM: Artificial
<220> FEATURE:
<223> OTHER INFORMATION: RT-PCR primer

<400> SEQUENCE: 15
ctcgtcctcc cattaatgta aaaa                                              24

<210> SEQ ID NO 16
<211> LENGTH: 24
<212> TYPE: DNA
<213> ORGANISM: Artificial
<220> FEATURE:
<223> OTHER INFORMATION: RT-PCR primer

<400> SEQUENCE: 16
tccagcttca ccagtttgga gtaa                                              24

<210> SEQ ID NO 17
<211> LENGTH: 19
<212> TYPE: DNA
<213> ORGANISM: Artificial
<220> FEATURE:
<223> OTHER INFORMATION: RT-PCR primer

<400> SEQUENCE: 17
cagatggact ttctggccg                                                    19

<210> SEQ ID NO 18
<211> LENGTH: 19
<212> TYPE: DNA
<213> ORGANISM: Artificial
<220> FEATURE:
<223> OTHER INFORMATION: RT-PCR primer

<400> SEQUENCE: 18
cttgagctgc tgcagcttc                                                    19

<210> SEQ ID NO 19
<211> LENGTH: 23
<212> TYPE: DNA
<213> ORGANISM: Artificial
<220> FEATURE:
<223> OTHER INFORMATION: RT-PCR primer

<400> SEQUENCE: 19
gaagcacctc aagcagcagc agg                                               23

<210> SEQ ID NO 20
<211> LENGTH: 25
<212> TYPE: DNA
<213> ORGANISM: Artificial
<220> FEATURE:
<223> OTHER INFORMATION: RT-PCR primer

<400> SEQUENCE: 20
cactctcttt gctcttctcc ttgtt                                             25

<210> SEQ ID NO 21
<211> LENGTH: 18
<212> TYPE: DNA
<213> ORGANISM: Artificial
<220> FEATURE:
<223> OTHER INFORMATION: RT-PCR primer

```
-continued

<400> SEQUENCE: 21
agctggctga agtgatcc                                                      18

<210> SEQ ID NO 22
<211> LENGTH: 18
<212> TYPE: DNA
<213> ORGANISM: Artificial
<220> FEATURE:
<223> OTHER INFORMATION: RT-PCR primer

<400> SEQUENCE: 22
tcaccatcag cctctgag                                                      18

<210> SEQ ID NO 23
<211> LENGTH: 21
<212> TYPE: DNA
<213> ORGANISM: Artificial
<220> FEATURE:
<223> OTHER INFORMATION: RT-PCR primer

<400> SEQUENCE: 23
tcagaggttc ctatgggcct g                                                  21

<210> SEQ ID NO 24
<211> LENGTH: 20
<212> TYPE: DNA
<213> ORGANISM: Artificial
<220> FEATURE:
<223> OTHER INFORMATION: RT-PCR primer

<400> SEQUENCE: 24
tggagacgtt ccactgaggg                                                    20
```